United States Patent [19]
Harris

[11] Patent Number: 5,700,781
[45] Date of Patent: Dec. 23, 1997

[54] METHOD FOR TREATING KAPOSI'S SARCOMA AND HIV INFECTIONS

[76] Inventor: Pamela Jo Harris, 4000 Massachusetts Ave., NW., Apt. 634, Washington, D.C. 20009

[21] Appl. No.: 338,166

[22] Filed: Nov. 10, 1994

Related U.S. Application Data

[63] Continuation of Ser. No. 317,909, Oct. 4, 1994, abandoned.

[51] Int. Cl.$^6$ .................... A61K 38/00; A61K 39/21; C07K 1/00
[52] U.S. Cl. .................... 514/21; 514/8; 514/12; 514/885; 514/934; 424/188.1; 424/208.1; 530/324; 530/397; 530/398; 530/399
[58] Field of Search .................... 514/21, 8, 12, 514/885, 934; 530/324, 397, 398, 399, 828; 424/188.1, 208.1

[56] References Cited

U.S. PATENT DOCUMENTS

| | | | |
|---|---|---|---|
| 4,692,332 | 9/1987 | McMichael | 424/88 |
| 4,877,610 | 10/1989 | McMichael | 424/88 |
| 4,880,626 | 11/1989 | McMichael | 424/88 |
| 4,966,753 | 10/1990 | McMichael | 424/88 |
| 4,970,071 | 11/1990 | McMichael | 424/88 |

OTHER PUBLICATIONS

Gold, Treatment Science, vol. 8, No. 7, pp. 1–2, 1994.
"New Directions Needed for AIDS Research," *Computer DIALOG PHIND* (Archival), Aug. 19, 1994.
Bourinbaiar et al, *FEBS. LETS.*, vol. 309, No. 1, pp. 82–84, Aug. 1992.
Lunardi–Iskandar et al, *Nature*, vol. 375, pp. 64–68, 4 May, 1995.
McNamee, *The Lancet*, vol. 345, p. 1169, May 6, 1995.
Harris, *The Lancet*, vol. 346, pp. 118–119, Jul. 8, 1995.
Overbeck et al, *The Lancet*, vol. 346, pp. 642–643, Sep. 2, 1995.
Monfardini et al. "Treatment of Acquired Immunodeficiency Syndrome (AIDS)–Related Cancer," *Cancer Treatment Reviews*, 20:149–72, 1994.
Lilenbaum et al. "Systemic Treatment of Kaposi's Sarcoma: Current Status and Future Directions," *AIDS*, 8:2;141–51, 1994.
"Immune Based Therapy Briefs," *PI Perspectives*, pp. 56, Nov. 1994.
Stein et al. "AIDS–Related Kaposi's Sarcoma: A Review," *Israel Journal of Medical Sciences*, 30:298, 1994.
Bourinbaiar et al. "Inhibitory Effect of Human Chorionic Gonadotropin (HCG) on HIV-1 Transmission from Lymphocytes to Trophoblasts," *FEBS LETS.*, 309:82, 1992.
Gold "Pregnancy Hormone Studied for KS," *Treatment Science*, 8:7;1–2, 1994.
Rosenthal et al. "Maladie de Kaposi et Hormones Sexuelle: `a Propos d'une Observation. Revue de la Littérature," *Rev. Méd. Interne*, 15:186–89, 1994 (English abstract).

*Primary Examiner*—Cecilia J. Tsang
*Assistant Examiner*—Abdel A. Mohamed
*Attorney, Agent, or Firm*—Foley & Lardner

[57] ABSTRACT

Prophylaxis against HIV, treatment for individuals infected with HIV, and treatment Kaposi's sarcoma can be effected, respectively, through the administration of human chorionic gonadotropin.

3 Claims, No Drawings

METHOD FOR TREATING KAPOSI'S SARCOMA AND HIV INFECTIONS

This is a continuation of application Ser. No. 08/317,909, filed Oct. 1, 1994, now abandoned.

BACKGROUND OF THE INVENTION

The present invention relates a treatment of Kaposi's sarcoma, and to a prophylactic intervention against and therapy for Human Immune Deficiency Virus I (HIV-1), the cause of Acquired Immune Difficiency Syndrome (AIDS).

Kaposi's sarcoma was originally described in 1872 by Dr. Moriz Kaposi, who identified a condition that involved the legs and feet of old Jewish men of Eastern European and Mediterranean descent. A more aggressive form of the disease was identified in African men in the early 1900s, and a third form was identified in transplant patients, specifically kidney recipients, in the 1970s. Subsequently, Kaposi's sarcoma was among the first described as a clinical manifestations of the Acquired Immune Deficiency Syndrome. Studies today demonstrate that up to 40% of homosexual men with AIDS develop Kaposi's sarcoma. One survey, reported in the Sep. 12, 1994 of *AIDS Weekly*, asserted that 49% of Los Angeles' AIDS patients had Kaposi's sarcoma at autopsy.

Patients with Acquired Immune Deficiency Syndrome (AIDS) both in the United States and in Europe are prone to develop malignancies, in particular Kaposi's sarcoma (Kaposi's sarcoma) and non-Hodgkins lymphoma. Monfardini, N. et al., *Cancer Treatment Reviews* (1994) 20:149–172. Kaposi's sarcoma is the most prevalent neoplasm of HIV-infected individuals. Recent review articles describing Kaposi's sarcoma include Lilenbaum, R. et al., *AIDS* (1994) 8:141–151, and Stein, M. et al., *Israel Journal of Medical Sciences* (1994) 30:298–305. All of the foregoing articles as well as all of the following articles, patents and patent applications expressly are incorporated herein by reference in their entireties.

Kaposi's sarcoma associated with AIDS consists of neoangiogenesis and dysplastic hyperplasia of endothelial cells. It generally presents as individual placque-like cutaneous tumors, often at the tips of the nose and ear lobes. Although often behaving like a late-opportunistic infection, it may present early in HIV infection when T4 cells are relatively high. When it spreads to visceral organs, such as lung parenchyma, prognosis for life is generally six months.

Treatment of AIDS-related Kaposi's sarcoma is fraught with problems. For patients with CD4 counts >400 cells/cmm, subcutaneous 60-interferon is considered to be standard therapy, however its administration is associated with flu-like symptoms including myalgia, arthralgia, low-grade fever, dysphoria and malaise mimicking and compounding the very problems experienced by those infected with HIV without Kaposi's sarcoma.

Chemotherapy with agents such as vincristine, adriamycin, and bleomycin is reasonable for disseminated Kaposi's sarcoma but has dose-limiting toxicities, which are particularly problematic for patients with AIDS. Reactions associated with painful neuropathy compounds already incapacitating peripheral, stocking-glove neuropathy typical of HIV and exacerbated by antivirals such as DDI, DDC, and D4T. Adriamycin induced myelosuppression and cardiomyopathic toxicity are particularly problematic for a patient population which is likely to be leukopenic pre-chemotherapy, as well as prone to HIV-cardiomyopathy. The anaphylaxis and pulmonary and cutaneous fibrosis associated with bleomycin can be formidable in a population fraught with pulmonary infections and dermatopathology. Radiation therapy, although clearly having a role in Kaposi's sarcoma, presents a challenge to both patient and physician. Cost also is often formidable; and scheduling time for daily radiotherapy imposes a major obstacle to maintaining quality of life, and such therapy may result in burns which become secondarily infected and become entry points for disseminated life-threatening infection.

While clinicians and basic scientists have wrestled with whether to classify AIDS-associated Kaposi's sarcoma as a malignancy or opportunistic infection, most now agree that it is a neoplasm. Ironically, the newly-described observations of the universal presence of β human gonadotropic hormone receptors strengthen the concept of the clonal; i.e., neoplastic, nature of AIDS-associated Kaposi's sarcoma.

Human chorionic gonadotropin (HCG) is a polypeptide produced by the human placenta and is composed of α and β subunits. The e chain of HCG is homologous with leutinizing hormone (LH), follicle-stimulating hormone (FSH), and thyroid-stimulating hormone (TSH); the β subunit is closest in structure to the β subunit of LH, however HCG acts biologically most like LH but with some FSH properties.

Scientifically elegant observations of the presence of HCG receptors on Kaposi's sarcoma cells as well as other elegant observations of the interplay of human reproductive endocrinology and Kaposi's sarcoma have emerged over the last two years. In the Sep. 1993 issue of *Treatment Science*, two pregnant women were noted to have "spontaneous resolution", of Kaposi's sarcoma. Dr. Robert Gallo, Chief of the Laboratory of Tumor Cell Biology of the National Cancer Institute, reported on Aug. 8, 1994 in Yokohama, Japan, that administration of HCG to nude mice infected with a tumor cell line derived from human Kaposi's sarcoma eradicated all evidence of this tumor in this murine model. Dr. Gallo et al. also noted that they were unable to grow this tumor cell line in a female mouse during the first trimester of the pregnancy. Administration of HCG in the range of 5–10 International Units (IU) per gram of mouse weight three times per week intramuscularly resulted in the regression of Kaposi's sarcoma in nude mice. See *Japan Science Scan*, Aug. 15, 1994.

Much of human reproductive function is controlled by the family of heterodimeric human glycoprotein hormones identified above. HCG itself is a water-soluble glycoprotein derived from human pregnancy urine. It is prepared for intramuscular injection as a sterile lyophilized powder. HCG is marketed by, e.g., Serono in vials containing either 5,000 or 10,000 USP Units.

During the normal menstrual cycle, LH participates with FSH in the development and maturation of the normal ovarian follicle and the mid-cycle LH surge triggers ovulation. HCG can substitute for LH in this function. During a normal pregnancy, HCG secreted by the placenta maintains the corpus luteum after LH secretion decreases, supporting continued secretion of estrogen and progesterone in preventing menstruation.

HCG also is present in certain tumors. For example, germ cell tumors have high levels of HCG. Other tumors, such as adenocarcinoma of the lung and pancreatic adenocarcinoma, also contain high HCG levels.

The role of the interplay of the endocrine system and the immune system in human reproduction and in human cancers has been given relatively little investigation. Attention to this hormonal-immunologic interplay may be vital to the successful treatment of HIV.

The interplay of various hormones in the context of treating Kaposi's sarcoma itself specifically is unclear. For example, notwithstanding the stimulation of androgens in males treated with HCG, Rosenthal, E. et al. (*Revue Medicale Interne* (1994) 15:186–189) reported that a 59-year-old bisexual man without HIV-1 or HIV-2 infection developed AIDS-related-like Kaposi's sarcoma while the patient was receiving both androgen and steroid therapy for aplastic anemia. The lesions regressed after interruption of therapy, despite the persistence of aplastic anemia.

Administration of Peptide T induced hormonal changes in AIDS patients that normalized subnormal testosterone levels, causing patients to experience a second puberty. The levels were maintained throughout therapy and were felt to be critical in the patients' positive response to Peptide T. Harris, P. "Peptide T and Male Sexuality", *AIDS Patient Care*, Feb. 1992; 6(1). Moreover, AIDS has been associated with diabetes insipidus, demonstrating another pituitary disfunction resulting from HIV infection. The present inventor reported further on the presence of diabetes in AIDS patients at the International AIDS conference in Yokohama Japan in August 1994.

Therapies for Kaposi's sarcoma have been sought and are critical to discover that would effect a cure, provide palliative relief or an extended period of remission but which would not present severe toxicities and complications in their own right.

SUMMARY OF THE INVENTION

It is therefore an object of the present invention to provide an effective approach to prophylaxis against HIV.

It is another object of the present invention to provide a method for treating HIV-infected individuals in order to eradicate the virus.

It is yet another object of the present invention to provide a treatment for Kaposi's sarcoma.

In accomplishing these and other objects, there has been provided, in accordance with one aspect of the present invention, a method for counteracting HIV in an individual infected with HIV or at risk from HIV infection, comprising the step of administering human chorionic gonadotropin (HCG) to the individual. In a preferred embodiment, the individual receives said HCG such that the individual has a blood level of HCG ranging between about 10,000 and about 300,000 IU per liter of blood.

According to another aspect of the present invention, a method is provided for treating Kaposi's sarcoma in an individual who has a Kaposi's tumor, comprising the administration of human chorionic gonadotropin (HCG) to the individual. Pursuant to a preferred embodiment, the individual receives an administration of 5,000 and 10,000 IU of HCG per kilogram of body weight, said administration being repeated three times per week.

DETAILED DESCRIPTION OF PREFERRED EMBODIMENTS

I have observed in my clinical practice that none of the patients with Kaposi's sarcoma have high serum levels of HCG. In contrast, I have observed that all patients with Kaposi's sarcoma have low serum levels of HCG. Through detailed observations of the immunoendocrine aspects of HIV infections, I surmised that administration of high doses of HCG would usefully treat Kaposi's sarcoma.

Thus, as a result of protocols beginning with doses of HCG at levels described below for the treatment of hypogonadotropic hypogonadism, and increasing these dosages substantially, my patients have experienced a rapid improvement in overall health and a regression of the Kaposi's sarcoma lesions. In addition, one patient with limited cutaneous Kaposi's was treated with moderate dose, intramuscular HCG, causing near total regression of the Kaposi's tumor. He was lost to follow up for several days and returned with massive new lesions, as well as an exacerbation of those that had been in near remission. With renewed treatment according to the present invention, all lesions regressed and no new lesions formed.

Furthermore, two patients who did not respond effectively to irradiation and chemotherapy, respectively, were treated with intramuscular HCG. The result in both cases was a regression of lesions.

As a rationale for these observations, it is noted that HCG receptors on the corpus luteum are activated by placental HCG. This in turn causes continued progesterone (and estrogen) secretion from the corpus luteum which directly (or perhaps indirectly, via HCG) allows endometrial vascular structural changes, i.e., decidual changes, to favor a normal pregnancy. In the same fashion, HCG receptors on Kaposi's Sarcoma cells are activated by exogenous HCG, which in turn allows normalization of vascular tissue in these vascular anaplastic cells. In essence, therefore, placental HCG changes endometrial vascular structure to provide a bed for normal fetal development, while exogenous HCG changes Kaposi's sarcoma cells from anaplastic (or dysplastic) to normal.

I have administered HCG to my patients that is marketed commercially by Serono, Inc., under the brand name PRO-FASI®. It also is marketed by Wyeth Ayerst, under the name PREGNYL, and there are other commercial sources for suitable HCG formulations.

Contraindications for HCG are precocious puberty, prostatic carcinoma or other androgen-dependent neoplasms and a prior allergic reaction to HCG. Adverse reactions include headache, irritability, restlessness, depression, fatigue, edema, precocious puberty, gynecomastia, pain at the site of injection as well as various hypersensitivity reactions. Administration of HCG according to the present invention should take into account these considerations.

I contemplate the administration of HCG, for an average patient of about 65 kg, in an amount of about 325,000 to about 650,000 IU/dose when HCG is administered three times per week. The administration of lower doses of HCG may be effective as well, but what is important is that the administration of HCG will cure Kaposi's sarcoma lesions and prevent the occurrence of additional lesions. Appropriate dosages for individual patients can be developed readily by those skilled in the art according to overall health indicators.

The following examples describe the clinical improvements of four HIV-infected patients with Kaposi's sarcoma treated in my practice. These examples are not intended to limit the scope of the invention in any way. For example,-it is contemplated that recombinant HCG or active fragments of HCG will provide the anti-Kaposi's sarcoma activity of the molecule isolated from human urine.

EXAMPLE 1

Patient KB

Patient KB was a 30 year old white male, diagnosed as having Kaposi's sarcoma about 10 months prior to the initiation of HCG therapy. Within three months the patient was placed on chemotherapy and received dosages approximately every three weeks for about five months. Combination chemotherapy was administered, specifically bleomycin, adriamycin (doxorubicin), and vincristine according to the standard 1987 protocol known to physicians who treat Kaposi's sarcoma. The therapy caused depression and myelosuppression. It resulted in minimal regression of existing lesions, but new lesions also appeared. Before the start of HCG therapy, Patient KB developed lesions on the back, face, neck and arms that were not present at beginning of chemotherapy.

The following dosages of HCG were administered IM according to the standard protocols for administration of this therapeutic on the following schedule: 1,000 IU (Day 1), 5,000 IU (Day 2), 8,000 IU (Day 3), 14,000 IU (Day 4), 20,000 IU (Day 5), 24,000 IU (Day 6), 30,000 IU (Day 7), 30,000 IU (Day 8), 50,000 IU (Day 9), 60,000 IU (Day 11), 70,000 IU (Day 12), 80,000 IU (Day 13), 90,000 IU (Day 14), 100,000 IU (Day 15), 150,000 IU (Day 18) and 162,000 IU (Day 19).

By Day 5 there were skin retractions of the circumference of lesions, reducing the size of the tumor. On Day 9, central clearing with central skin retraction was observed. There also was a lightening of erythema in the remaining lesions. By Day 19 some large, flat lesions had become small, nodular lesions, while others cleared completely. There were small, petechial lesions in some of the tissue were Kaposi's sarcoma had been present.

EXAMPLE 2

Patient MH

The following dosages of HCG were administered IM according to the standard protocols for administration of this therapeutic on the following schedule: 5,000 IU (Day 1), 10,000 IU (Day 2), 20,000 IU (Day 3), 30,000 IU (Day 4), 40,000 IU (Day 5), 60,000 IU (Day 8), 80,000 IU (Day 9), and 120,000 IU (Day 14).

The patient responded.well, with tumor regression observed, but was lost to follow up. The result was a reappearance of old lesions and aggressive formation of new lesions. Resumption of treatment, now at 300,000 IU per day, resulted in a total regression of original lesions, marked diminution of lesions which had developed off therapy, and an observation of no new lesions.

EXAMPLE 3

Patient BW

Patient BW is a 39 year old white male, diagnosed as being HIV positive about eight years prior to receiving HCG therapy for Kaposi's sarcoma. About 30 months prior to receiving HCG therapy, Patient BW was treated with chemotherapy for Kaposi's sarcoma lesions on his legs. Chemotherapy was restarted about six months later and continued for about two months. The patient received combined chemotherapy for about the nine months preceding initiation of HCG therapy. His lesions were generally flat in profile. Chemotherapy appeared to prevent spread of the lesions, but did not appear to cause them to regress. About one month before HCG therapy, this patient began to experience nausea, vomiting, depression and hair loss, and developed stomatitis. He also had hypogonadotropic hypogonadism.

The following dosages of HCG were administered IM according to the standard protocols for administration of this therapeutic on the following schedule: 1,000 IU (Day 1), 1,000 IU (Day 3), 5,000 IU (Day 7), 7,500 IU (Day 8), 9,000 IU (Day 9), 9,000 IU (Day 10), 13,000 IU (Day 11), 17,000 IU (Day 12), 20,000 IU (Day 14), 20,000 IU (Day 15), 20,000 IU (Day 16), 22,000 IU (Day 17), 24,000 IU (Day 18), 28,000 IU (Day 22), 30,000 IU (Day 23), 30,000 IU (Day 24), 40,000 IU (Day 26), 50,000 IU (Day 28), 60,000 IU (Day 29), 80,000 IU (Day 31), 90,000 IU (Day 32), 50,000 IU (Day 33), 120,000 IU (Day 35), 150,000 IU (Day 37), 180,000 IU (Day 39) and 200,000 IU (Day 42).

By Day 35, almost all of BW's lesions were significantly lighter in color and decreasing in size. The patient also reported a much higher energy level.

EXAMPLE 4

Patient LM

Patient LM is a 44 year old white male with AIDS. About eight months prior to beginning HCG therapy, this patient presented with a 1×1.5 cm area of redness on the right anterior neck. One month later, this area had changed into a 2×1 cm red placque with some nodularity. After local radiation treatment, the lesion regrew. The patient also had developed hypogonadotropic hypogonadism by the time that HCG therapy was commenced.

The following dosages of HCG were administered IM according to the standard protocols for administration of this therapeutic on the following schedule: 5,000 IU (Day 1), 10,000 IU (Day 2), 20,000 IU (Day 3), 30,000 IU (Day 4), 40,000 IU (Day 5), 25,000 IU (Day 6), 60,000 IU (Day 8) and 80,000 IU (Day 9).

I observed that by Day 5, the lesion had undergone central clearing. By Day 20 the lesion was markedly decreased in size., and what remained was extremely pale and flat.

The foregoing examples present clinical findings of several AIDS patients who have been treated with elevated dosages of HCG in connection with therapy for Kaposi's sarcoma. The present invention is not limited, however, to AIDS-related Kaposi's sarcoma, but rather can be used generally to treat the cancer. In this regard I contemplate that an optimum treatment schedule would be to administer HCG about three times per week, as discussed above.

In appropriate formulations that are known and conventional to those skilled in the art, the administration of HCG by various routes of administration is contemplated, including intramuscular, oral, subcutaneous, transmucosal, transdermal and parenteral. Administration of HCG specifically is contemplated through a timed-release drug delivery system, e.g., transdermal skin patches, such as are well-known to physicians and those skilled in the relevant art. Exemplary devices (not to be considered limitative of the present invention) are disclosed, e.g., in U.S. Pat. Nos. 5,316,759, 5,324,521, 5,326,570, 5,332,577, 5,336,213, 5,336,505, 5,344,656, 5,346,701 and 5,350,581.

According to another embodiment of the present invention, HCG is given at an appropriate dose through an effective delivery system to prevent transmission of HIV and to kill HIV in individuals already infected. While the invention is not limited by the mechanism(s) underlying effectiveness in this regard, it is believed that HCG administered according to the present invention inhibits reverse transcriptase or alters thymic function.

More specifically, it has been discovered that HCG inhibits HIV infection, via immune mechanisms such as occupying receptors on the thymus or via inhibition of viral reverse transcriptase. This explains why pregnant women who produce very high levels of HCG in their first trimester of pregnancy do not transmit HIV to their fetuses during this time period. HCG-mediated reversal of HIV-positive, maternal lymphocytes and monocytes to negatives prevents transmission of HIV infected cells to the fetus. After the normal LH surge and LH decline in the mother, placental HCG is produced, maintaining corpus luteum secretory activity and allowing appropriate vascularization (decidual changes) in the endometrium to maintain pregnancy.

AccordingLy, "appropriate dose" in the context of the present invention is guided by the observation that AIDS never occurs during the first trimester of pregnancy, and only rarely during the second and third trimesters. Blood levels of HCG between 10,000 and 300,000 IU per liter of blood are typically seen in a mother's blood during the first three months of gestation, falling to 20,000 to 40,000 IU during the last six months of gestation. At partruition and the delivery of a placenta, there is a massive decline in HCG, and baby is rendered at risk to acquire HIV.

Illuminated by this understanding, the present contemplates HCG administration to HIV-infected individuals, or to individuals at risk to develop AIDS, such that blood levels are maintained at 10,000 to 300,000 IU per liter of blood, more preferably on the order of 100,000 IU per liter of blood, i.e., in the same range of maternal HCG levels during the first trimester of pregnancy. To achieve such levels according to the present invention, HCG can be administered intramuscularly but not without the technical difficulties associated with multiple injections. More preferred approaches to this end include a transdermal HCG patch and an implantable HCG delivery system, for example, a device such as NORPLANT®.

A bioavailable, sustained-release oral formulation of HCG also is possible. In addition, recombinant HCG should be feasible for human administration in this regard, allowing for an HCG-containing product that is purer, more concentrated and easier to administer.

What is claimed is:

1. A method of treating an individual infected with HIV comprising the step of administering an amount of human chorionic gonadotropin (HCG) such that said individual has a blood level of HCG of at least 10,000 IU per liter of blood is attained.

2. A method for treating Kaposi' sarcoma in an individual, comprising the administration of human chorionic gonadotropin (HCG).

3. A method according to claim 2, wherein said individual is administered a dosage of HCG comprising at least 5,000 IU per kilogram of body weight, said dosage being administered to said individual at least three times a week.

* * * * *